(12) United States Patent
Ohtsubo et al.

(10) Patent No.: US 9,229,047 B2
(45) Date of Patent: Jan. 5, 2016

(54) METHOD FOR MANUFACTURING SENSOR ELEMENT FOR USE IN GAS SENSOR, INSPECTING ELECTRICAL CHARACTERISTICS OF SENSOR ELEMENT, AND PRE-TREATING SENSOR ELEMENT

(71) Applicant: NGK INSULATORS, LTD., Nagoya (JP)

(72) Inventors: Shinji Ohtsubo, Nagoya (JP); Tetsuya Ishikawa, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 126 days.

(21) Appl. No.: 13/798,496

(22) Filed: Mar. 13, 2013

(65) Prior Publication Data

US 2013/0255352 A1  Oct. 3, 2013

(30) Foreign Application Priority Data

Mar. 29, 2012  (JP) ................................. 2012-076391

(51) Int. Cl.
| | |
|---|---|
| G01N 27/406 | (2006.01) |
| G01N 27/407 | (2006.01) |
| G01N 27/409 | (2006.01) |
| G01N 27/41 | (2006.01) |
| G01R 31/28 | (2006.01) |
| G01R 35/00 | (2006.01) |

(52) U.S. Cl.
CPC ............ *G01R 31/28* (2013.01); *G01N 27/4071* (2013.01); *G01R 35/00* (2013.01); *G01N 27/4074* (2013.01); *Y10T 29/49002* (2015.01); *Y10T 29/49004* (2015.01)

(58) Field of Classification Search
CPC ............ G01N 33/0006; G01N 33/007; G01N 27/4175
See application file for complete search history.

(56) References Cited

U.S. PATENT DOCUMENTS

| | | | |
|---|---|---|---|
| 5,902,469 A | 5/1999 | Kato et al. | |
| 6,266,993 B1 * | 7/2001 | Diehl et al. | ..................... 73/1.06 |
| 6,471,840 B1 * | 10/2002 | Gao et al. | ....................... 204/425 |
| 2009/0242403 A1 * | 10/2009 | Suzuki et al. | .................. 204/431 |
| 2011/0138875 A1 | 6/2011 | Shindo et al. | |

FOREIGN PATENT DOCUMENTS

| | | | | |
|---|---|---|---|---|
| EP | 2058653 A1 * | 5/2009 | ........... | G01N 27/419 |
| JP | 2000-180400 A | 6/2000 | | |

(Continued)

OTHER PUBLICATIONS

Japanese Office Action, Japanese Application No. 2012-076391, dated Apr. 1, 2014 (3 pages).

*Primary Examiner* — Eric S McCall
*Assistant Examiner* — Anthony W Megna Fuentes
(74) *Attorney, Agent, or Firm* — Burr & Brown, PLLC

(57) ABSTRACT

To provide a method for manufacturing a sensor element, by which stabilization of an electrode, which is performed prior to inspecting element characteristics, can be performed for a shorter time period and in a more reliable manner than in the conventional. The sensor element includes: an oxygen-ion conductive solid electrolyte layer; a first electrode that is formed on a surface of the oxygen-ion conductive solid electrolyte layer; and a second electrode that is formed in a space provided inside the oxygen-ion conductive solid electrolyte layer, and that is configured to reduce said predetermined gas component. As the pre-treatment, by an external power source, a voltage is applied between the first electrode and the second electrode, to thereby decompose and remove a gas component attached to the second electrode.

6 Claims, 11 Drawing Sheets

(56) References Cited

FOREIGN PATENT DOCUMENTS

| JP | 3537983 | B2 | 6/2004 |
| JP | 2004-294079 | A | 10/2004 |
| JP | 2006-284223 | A1 | 10/2006 |
| JP | 2011-145285 | A1 | 7/2011 |
| JP | 4826566 | B2 | 11/2011 |

* cited by examiner

F I G. 4
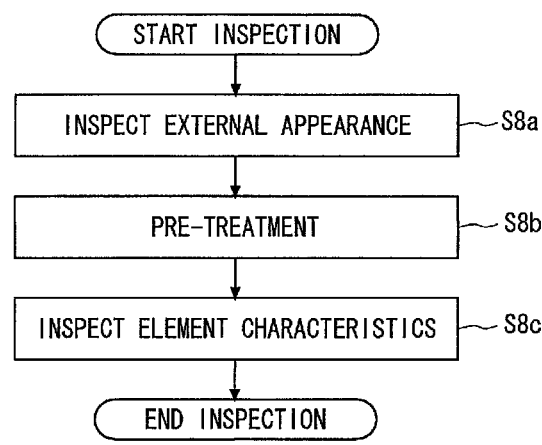

F I G. 1 3
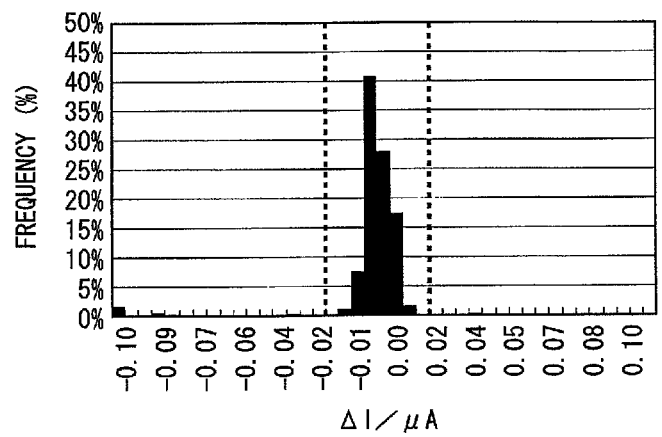
F I G. 1 4
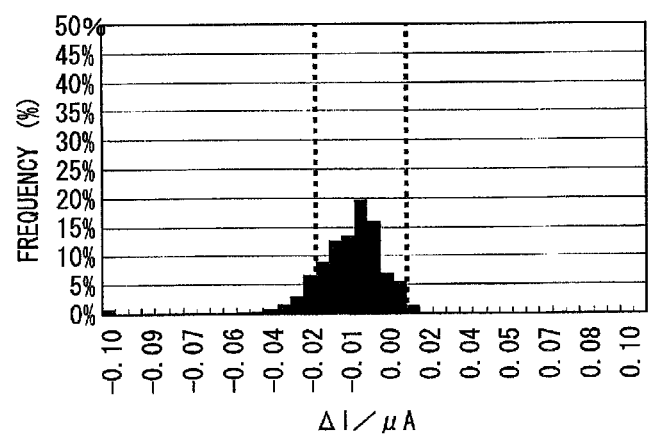

METHOD FOR MANUFACTURING SENSOR ELEMENT FOR USE IN GAS SENSOR, INSPECTING ELECTRICAL CHARACTERISTICS OF SENSOR ELEMENT, AND PRE-TREATING SENSOR ELEMENT

BACKGROUND OF THE INVENTION

1. Field of the Invention

The present invention relates to a method for manufacturing a sensor element for use in a gas sensor, and particularly to a method for stabilizing the condition of an electrode.

2. Description of the Background Art

Conventionally, various gas sensors have been used for recognizing a concentration of a desired gas component in a measurement gas. For example, as a device for measuring a NOx concentration in a measurement gas such as a combustion gas, known is a NOx sensor having a sensor element which is formed using an oxygen-ion conductive solid electrolyte such as zirconia ($ZrO_2$) (for example, see Japanese Patent Application Laid-Open No. 2006-284223 and Japanese Patent No. 3537983).

In sensor elements of gas sensors including the NOx sensors disclosed in Japanese Patent Application Laid-Open No. 2006-284223 and Japanese Patent No. 3537983, a concentration of a measurement object gas component (object component) is obtained by utilizing the fact that in a case where the measurement object gas component is decomposed at a measuring electrode by the catalytic activity thereof, the amount of oxygen ion occurring at that time is proportional to a current flowing in the measuring electrode and a reference electrode. To be specific, a concentration value of the object component is recognized as follows: a relationship (sensitivity characteristics, a concentration profile) between a concentration value and a current value (output signal value) in each individual sensor element is obtained in advance by using a mixed gas whose object component concentration is already known; and in an actual use, a measured current value is converted into a concentration value based on the sensitivity characteristics.

Therefore, it is ideal that the current value is zero in a case where the object component does not exist in the measurement gas. However, actually, oxygen originally existing in the measurement gas is, though removed prior to the decomposition of the object gas component, left in a small amount and is decomposed, so that a current slightly flows. Accordingly, it is normal that prior to use, a current value (derived from residual oxygen and the like) under a state where the object component does not exist is identified as an offset value, and a value obtained by subtracting the offset value from a current value obtained under a state where the object component exists is used as a current value which is proportional to a gas concentration.

The above-mentioned sensitivity characteristics are determined before each gas sensor is used (for example, before shipment), and normally dealt as fixed characteristics without being changed when the gas sensor is used afterward. This is based on the assumption that actual sensitivity characteristics do not vary during the use of the gas sensor. If the actual sensitivity characteristics change over time, the concentration value which is calculated based on the sensitivity characteristics determined at the time of shipment loses its reliability as the use of the gas sensor continues, and eventually the gas sensor loses a measurement accuracy set in its specification.

However, the condition of an electrode of a sensor element obtained after an aging process is not stabilized because, for example, the degree of oxidation during baking of the element and the degree of reduction during the aging in a rich atmosphere, which is performed after the baking, are not constant, and a rich component that is left within the sensor element after the aging is suddenly decomposed. In other words, this means that the catalytic activity of the measuring electrode varies among sensor elements before they are shipped. Inspecting the element characteristics and further determining the sensitivity characteristics under such an unstabilized state may cause an erroneous determination in which a sensor element that is actually a non-defective product is determined as a defective product. This results in a reduction in the production yield. In view of this point, a technique is already known in which the condition of an electrode is stabilized by performing, prior to inspecting the element characteristics, a pre-treatment process for driving the sensor element in advance for a predetermined time period in a mixed gas atmosphere that is similar to an actual usage environment (for example, see Japanese Patent Application Laid-Open No. 2011-145285).

The pre-treatment method disclosed in Japanese Patent Application Laid-Open No. 2011-145285 exerts an effect of stabilizing the electrode of the sensor element, but the effect is not always constant. Thus, there is a problem that an improvement in the production yield is limited. Additionally, there is also a problem that this method cannot always be regarded as a satisfactory method from the viewpoint of the productivity of the sensor element, because it is necessary to drive the sensor element in the mixed gas atmosphere though the time period thereof is merely about ten minutes. Although it is possible to perform the pre-treatment by an apparatus configured to inspect the element characteristics, this is not always preferable from the viewpoint of the productivity of the sensor element, because, in such a case, the inspection of the element characteristics cannot be performed during the time period of the pre-treatment. On the other hand, using a special apparatus for performing the pre-treatment causes a problem that the size of an apparatus is increased because the gas is used, resulting in an increased cost.

SUMMARY OF THE INVENTION

The present invention relates to a method for processing a sensor element for use in a gas sensor, and particularly to stabilization of the condition of an electrode, which is performed prior to inspection of element characteristics.

In the present invention, a method for manufacturing a sensor element for use in a gas sensor that measures a concentration of a predetermined gas component in a measurement gas includes the following steps, wherein the sensor element includes an electrochemical pumping cell including: an oxygen-ion conductive solid electrolyte layer, a first electrode that is formed on a surface of the oxygen-ion conductive solid electrolyte layer, and a second electrode that is formed in a space provided inside the oxygen-ion conductive solid electrolyte layer: a) forming, by printing, a wiring pattern of a conductive paste on a green sheet containing, as a main component, ceramic which is an oxygen-ion conductive solid electrolyte, the wiring pattern including portions serving as the first electrode and the second electrode; b) laminating a plurality of green sheets that have been subjected to the step a), and integrating the plurality of green sheets; c) cutting out a plurality of element bodies from a laminated body obtained by the step b); d) baking the element body cut out by the step c); e) heating the element body having been subjected to the step d), in a reducing atmosphere; f) by an external power source, applying a voltage between the first electrode and the second electrode included in the element body having been subjected to the step e), to thereby decompose and remove an atmosphere gas of the step e) attached to the second electrode; and g) inspecting electrical characteristics of the element body having been subjected to the step f).

Prior to inspecting the electrical characteristics of the sensor element in the step g), the voltage is applied between the first electrode and the second electrode included in the sensor element to thereby decompose and remove a gas component attached to the second electrode in the step f). This enables the inspection of element characteristics in the step g) to be performed under a state where the condition of the electrodes is stabilized. This can prevent, in the inspection of element characteristics, occurrence of an erroneous decision which determines that a sensor element which should be determined to be a non-defective product is a defective product. Additionally, sensitivity characteristics can be surely determined with a reliability. Thus, the production yield can be improved, and a gas sensor having a high reliability can be achieved.

Therefore, an object of the present invention is to provide a method for treating a sensor element, by which stabilization of an electrode, which is performed prior to inspecting element characteristics, can be performed for a shorter time period and in a more reliable manner than in the conventional.

BRIEF DESCRIPTION OF THE DRAWINGS

FIG. 4 is a diagram showing a flow of an inspection step.

FIG. 13 is a histogram of the value of ΔI, which is obtained in a case of inspecting the element characteristics after performing the pre-treatment.

FIG. 14 is a histogram of the value of ΔI, which is obtained in a case of inspecting the element characteristics after performing a gas pre-treatment.

DETAILED DESCRIPTION OF THE INVENTION

<Outline Configuration Of Gas Sensor>

Figure 1:
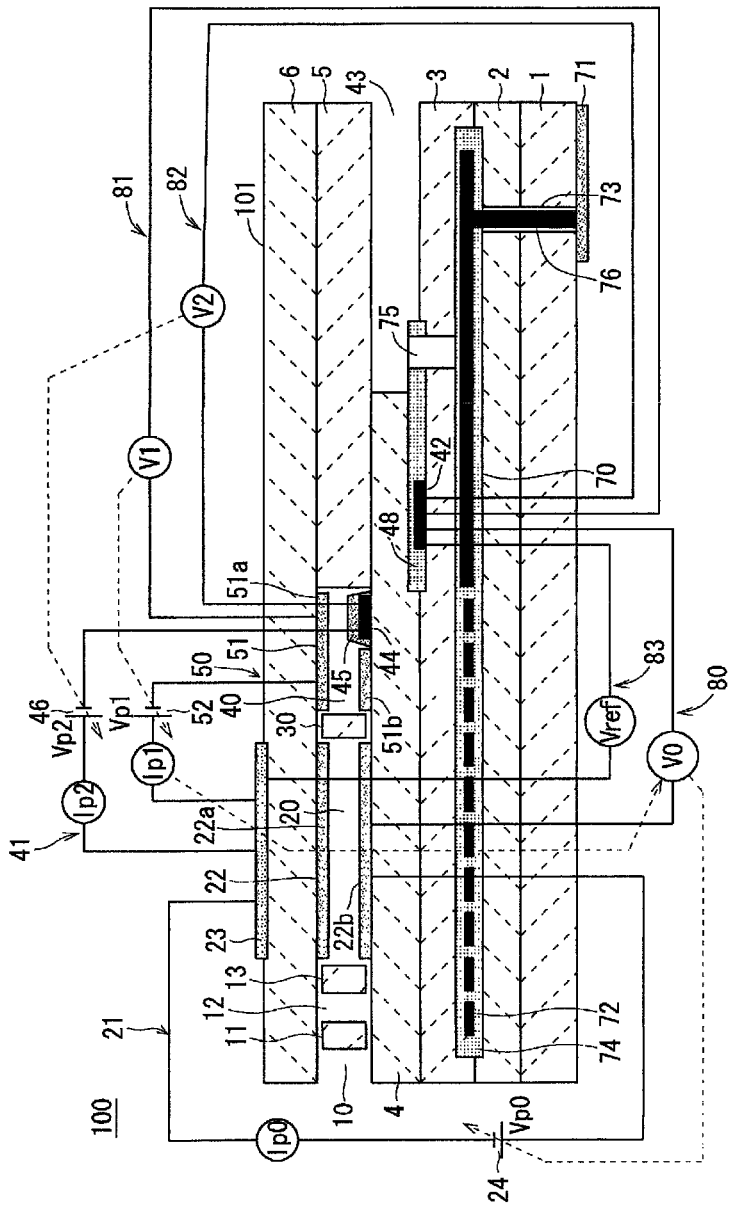
FIG. 1 is a schematic cross-sectional view showing an outline of an exemplary configuration of a gas sensor 100.

FIG. 1 is a schematic cross-sectional view showing an outline of an exemplary configuration of a gas sensor 100. A sensor element 101 has a structure in which six layers, namely, a first substrate layer 1, a second substrate layer 2, a third substrate layer 3, a first solid electrolyte layer 4, a spacer layer 5, and a second solid electrolyte layer 6, are laminated in the mentioned order from the bottom side seen in FIG. 1, each of the layers being fainted by an oxygen-ion conductive solid electrolyte such as a zirconia ($ZrO_2$). The solid electrolyte forming these six layers is densely airtight. The sensor element 101 is manufactured by, for example, performing a predetermined process and printing a circuit pattern on ceramic green sheets, each of which corresponds to each of the layers, then laminating the green sheets, and furthermore baking the laminated body to integrate it.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40, are adjacently formed in the mentioned order so as to be in communication with one another.

The gas inlet 10, the buffer space 12, the first internal space 20, and the second internal space 40 are spaces within the sensor element 101 provided by hollowing out the spacer layer 5, in which their upper portions are defined by the lower surface of the second solid electrolyte layer 6, their lower portions are defined by the upper surface of the first solid electrolyte layer 4, and their side portions are defined by a side surface of the spacer layer 5.

Each of the first diffusion control part 11, the second diffusion control part 13, and the third diffusion control part 30 is provided as two horizontally long slits (whose openings are elongated in a direction perpendicular to the plane of the drawing sheet of FIG. 1). A part extending from the gas inlet 10 to the second internal space 40 is also referred to as a gas distribution part.

At a position which is farther from the end portion than the gas distribution part is, a reference gas inlet space 43 is provided between an upper surface of the third substrate layer 3 and a lower surface of the spacer layer 5. A side portion of the reference gas inlet space 43 is defined by a side surface of the first solid electrolyte layer 4. As a reference gas for measuring a NOx concentration, for example, air is introduced into the reference gas inlet space 43.

An air introduction layer 48 is constituted by porous alumina. The reference gas is introduced through the reference gas inlet space 43 into the air introduction layer 48. The air introduction layer 48 is formed so as to cover a reference electrode 42.

The reference electrode 42 is an electrode formed so as to be interposed between the upper surface of the third substrate layer 3 and the first solid electrolyte layer 4. As described above, the air introduction layer 48 leading to the reference gas inlet space 43 is provided around the reference electrode 42. By using the reference electrode 42, an oxygen concentration (oxygen partial pressure) in the first internal space 20 or the second internal space 40 can be measured, as will be described later.

In the gas distribution part, the gas inlet 10 is open to the outside, and a measurement gas is taken into the sensor element 101 from the outside through the gas inlet 10.

The first diffusion control part 11 applies a predetermined diffusion resistance to the measurement gas taken through the gas inlet 10.

The buffer space 12 is provided in order to guide the measurement gas introduced from the first diffusion control part 11, to the second diffusion control part 13.

The second diffusion control part 13 applies a predetermined diffusion resistance to the measurement gas introduced from the buffer space 12 into the first internal space 20.

When the measurement gas is introduced from the outside of the sensor element 101 into the first internal space 20, the measurement gas which was abruptly taken into the sensor element 101 through the gas inlet 10 due to a pressure fluctuation of the measurement gas existing in the outside (a pulsation of exhaust gas pressure, in a case where the measurement gas is an automobile exhaust gas) is not directly introduced into the first internal space 20, but is introduced into the first internal space 20 after a concentration fluctuation in the measurement gas is cancelled through the first diffusion control part 11, the buffer space 12, and the second diffusion control part 13. As a result, the concentration fluctuation in the measurement gas introduced into the first internal space 20 is reduced to as small as negligible.

The first internal space 20 is provided as a space for adjusting oxygen partial pressure in the measurement gas introduced through the second diffusion control part 13. The oxygen partial pressure is adjusted by the operation of a main pumping cell 21.

The main pumping cell 21 is an electrochemical pumping cell constituted by an inside pump electrode 22, an outside pump electrode 23, and a part of the second solid electrolyte layer 6 interposed between these electrodes. The inside pump electrode 22 has a ceiling electrode portion 22a provided on a substantially entire part of the lower surface of the second solid electrolyte layer 6 facing the first internal space 20. The outside pump electrode 23 is provided in a region on an upper surface of the second solid electrolyte layer 6 corresponding to the ceiling electrode portion 22a, so as to be exposed to the outside.

The inside pump electrode 22 is formed over the upper and lower solid electrolyte layers (the second solid electrolyte layer 6 and the first solid electrolyte layer 4) which define the first internal space 20, and the spacer layer 5 which provides a side wall to the first internal space 20. To be specific, the ceiling electrode portion 22a is formed on the lower surface of the second solid electrolyte layer 6 which provides a ceiling surface to the first internal space 20. A bottom electrode portion 22b is formed on the upper surface of the first solid electrolyte layer 4 which provides a bottom surface to the first internal space 20. A side electrode portion (not shown) connecting the ceiling electrode portion 22a to the bottom electrode portion 22b is formed on side wall surfaces (inner surfaces) of the spacer layer 5 which forms both side wall portions of the first internal space 20. Thus, the inside pump electrode 22 has a tunnel-like shape at a location where the side electrode portion is disposed.

Each of the inside pump electrode 22 and the outside pump electrode 23 is formed as a porous cermet electrode (for example, a cermet electrode including Pt containing Au by 1% and zirconia). The inside pump electrode 22 which is brought into contact with the measurement gas is formed using a material having a weakened reduction ability with respect to a NOx component in the measurement gas.

In the main pumping cell 21, a desired pump voltage Vp0 is applied between the inside pump electrode 22 and the outside pump electrode 23 to cause a pump current Ip0 to flow in a positive direction or a negative direction between the inside pump electrode 22 and the outside pump electrode 23, and this allows oxygen existing within the first internal space 20 to be pumped out to the outside or oxygen existing in the outside to be pumped into the first internal space 20.

In order to detect an oxygen concentration (oxygen partial pressure) in the atmosphere of the first internal space 20, an electrochemical sensor cell, in other words, a main-pump-controlling oxygen-partial-pressure detection sensor cell 80, is formed with the inside pump electrode 22, the second solid electrolyte layer 6, the spacer layer 5, the first solid electrolyte layer 4, the third substrate layer 3, and the reference electrode 42.

The oxygen concentration (oxygen partial pressure) in the first internal space 20 can be recognized by measuring an electromotive force V0 of the main-pump-controlling oxygen-partial-pressure detection sensor cell 80. Moreover, the pump current Ip0 is controlled by performing a feedback control on Vp0 such that the electromotive force V0 is maintained constant. Thereby, the oxygen concentration in the first internal space 20 can be maintained at a predetermined constant value.

The third diffusion control part 30 applies a predetermined diffusion resistance to the measurement gas whose oxygen concentration (oxygen partial pressure) has been controlled in the first internal space 20 by the operation of the main pumping cell 21, and guides the measurement gas to the second internal space 40.

The second internal space 40 is provided as a space for performing a process of measurement of a nitrogen oxide (NOx) concentration in the measurement gas that is introduced through the third diffusion control part 30. The measurement of the NOx concentration is performed mainly in the second internal space 40 in which the oxygen concentration has been adjusted by an auxiliary pumping cell 50. The NOx concentration is measured by an operation of a measuring pumping cell 41.

In the second internal space 40, the auxiliary pumping cell 50 performs further adjustment of oxygen partial pressure on the measurement gas whose oxygen concentration (oxygen partial pressure) has been adjusted in advance in the first internal space 20 and which has then been introduced through the third diffusion control part 30. This enables an oxygen concentration in the second internal space 40 to be maintained constant with a high accuracy. Therefore, the gas sensor 100 can measure a NOx concentration with a high accuracy.

The auxiliary pumping cell 50 is an auxiliary electrochemical pumping cell constituted by an auxiliary pump electrode 51, the outside pump electrode 23 (not limited to the outside pump electrode 23 but may be an appropriate electrode positioned outside the sensor element 101), and the second solid electrolyte layer 6. The auxiliary pump electrode 51 has a ceiling electrode portion 51a provided on a substantially entire part of the lower surface of the second solid electrolyte layer 6 facing the second internal space 40.

Similarly to the inside pump electrode 22 provided in the first internal space 20, the auxiliary pump electrode 51 has a tunnel-like shape and provided in the second internal space 40. That is, the ceiling electrode portion 51a is formed on the second solid electrolyte layer 6 which provides a ceiling surface to the second internal space 40. A bottom electrode portion 51b is formed on the first solid electrolyte layer 4 which provides a bottom surface to the second internal space 40. A side electrode portion (not shown) connecting the ceiling electrode portion 51a to the bottom electrode portion 51b is formed on both wall surfaces of the spacer layer 5 which provides side walls to the second internal space 40.

Similarly to the inside pump electrode 22, the auxiliary pump electrode 51 is formed using a material having a weakened reduction ability with respect to a NOx component in the measurement gas.

In the auxiliary pumping cell 50, a desired voltage Vp1 is applied between the auxiliary pump electrode 51 and the outside pump electrode 23, and this allows oxygen existing in the atmosphere of the second internal space 40 to be pumped out to the outside or oxygen existing in the outside to be pumped into the second internal space 40.

In order to control oxygen partial pressure in the atmosphere of the second internal space 40, an electrochemical sensor cell, in other words, an auxiliary-pump-controlling oxygen-partial-pressure detection sensor cell 81, is formed with the auxiliary pump electrode 51, the reference electrode 42, the second solid electrolyte layer 6, the spacer layer 5, the first solid electrolyte layer 4, and the third substrate layer 3.

A variable power source 52 causes the auxiliary pumping cell 50 to perform pumping. The variable power source 52 is voltage-controlled based on an electromotive force V1 which is detected by the auxiliary-pump-controlling oxygen-partial-pressure detection sensor cell 81. Therefore, the oxygen partial pressure in the atmosphere of the second internal space 40 is controlled down to such a partial pressure that gives substantially no influence on the NOx measurement.

At the same time, a pump current Ip1 of the auxiliary pumping cell 50 is used for a control of the electromotive force of the main-pump-controlling oxygen-partial-pressure detection sensor cell 80. Specifically, the pump current Ip1 is inputted as a control signal to the main-pump-controlling oxygen-partial-pressure detection sensor cell 80, and its electromotive force V0 is controlled, so that a gradient of the oxygen partial pressure in the measurement gas introduced through the third diffusion control part 30 into the second internal space 40 is maintained so as to be always constant. In a use as a NOx sensor, the oxygen concentration in the second internal space 40 is maintained at a constant value of approximately 0.001 ppm, by the operations of the main pumping cell 21 and the auxiliary pumping cell 50.

The measuring pumping cell 41 measures the NOx concentration in the measurement gas within the second internal space 40. The measuring pumping cell 41 is an electrochemical pumping cell constituted by the measuring electrode 44, the outside pump electrode 23, the second solid electrolyte layer 6, the spacer layer 5, and the first solid electrolyte layer 4. The measuring electrode 44 is provided on a part of the upper surface of the first solid electrolyte layer 4 facing the second internal space 40, and positioned apart from the third diffusion control part 30.

The measuring electrode 44 is a porous cermet electrode. The measuring electrode 44 also functions as a NOx reducing catalyst that reduces NOx existing in the atmosphere of the second internal space 40. The measuring electrode 44 is covered with a fourth diffusion control part 45.

The fourth diffusion control part 45 is a film constituted by a porous body containing alumina ($Al_2O_3$) as its main component. The fourth diffusion control part 45 serves to limit the amount of NOx that flows into the measuring electrode 44, and also functions as a protective film of the measuring electrode 44.

The measuring pumping cell 41 is able to pump out oxygen generated by decomposition of nitrogen oxide in the atmosphere around the measuring electrode 44, which is caused by the catalytic activity of the measuring electrode 44, and to detect the amount of the generated oxygen as a pump current (also called a NOx current) Ip2.

In order to detect oxygen partial pressure around the measuring electrode 44, an electrochemical sensor cell, in other words, a measuring-pump-controlling oxygen-partial-pressure detection sensor cell 82, is formed with the second solid electrolyte layer 6, the spacer layer 5, the first solid electrolyte layer 4, the third substrate layer 3, the measuring electrode 44, and the reference electrode 42. The variable power source 46 is controlled based on an electromotive force V2 detected by the measuring-pump-controlling oxygen-partial-pressure detection sensor cell 82.

The measurement gas introduced into the second internal space 40, in which the oxygen partial pressure has been controlled, reaches the measuring electrode 44 through the fourth diffusion control part 45. Nitrogen oxide in the measurement gas around the measuring electrode 44 is reduced ($2NO \rightarrow N2+O2$), to generate oxygen. The generated oxygen is pumped by the measuring pumping cell 41. At this time, a voltage Vp2 of the variable power source is controlled such that a control voltage V2 detected by the measuring-pump-controlling oxygen-partial-pressure detection sensor cell 82 is maintained constant. The amount of oxygen generated around the measuring electrode 44 is proportional to a nitrogen-oxide concentration in the measurement gas. Thus, the nitrogen-oxide concentration in the measurement gas is calculated by using the pump current Ip2 of the measuring pumping cell 41.

If the measuring electrode 44, the first solid electrolyte layer 4, the third substrate layer 3, and the reference electrode 42 are combined to form an electrochemical sensor cell functioning as oxygen-partial-pressure detection means, an electromotive force in accordance with a difference between the amount of oxygen generated by the reduction of a NOx component in the atmosphere around the measuring electrode 44 and the amount of oxygen contained in a reference atmosphere can be detected. Thereby, a concentration of the NOx component in the measurement gas can be obtained.

An electrochemical sensor cell 83 is formed with the second solid electrolyte layer 6, the spacer layer 5, the first solid electrolyte layer 4, the third substrate layer 3, the outside pump electrode 23, and the reference electrode 42. By an electromotive force $V_{ref}$ obtained by the sensor cell 83, oxygen partial pressure in the measurement gas existing in the outside of the sensor can be detected.

In the gas sensor 100 having the above-described structure, by operating the main pumping cell 21 and the auxiliary pumping cell 50, the measurement gas whose oxygen partial pressure is always maintained at a constant low value (having substantially no influence on the NOx measurement) is given to the measuring pumping cell 41. Accordingly, the NOx concentration in the measurement gas can be recognized based on the pump current Ip2 which flows as a result of the oxygen generated by the reduction of NOx being pumped out by the measuring pumping cell 41, substantially in proportion to the NOx concentration in the measurement gas.

Figure 2:
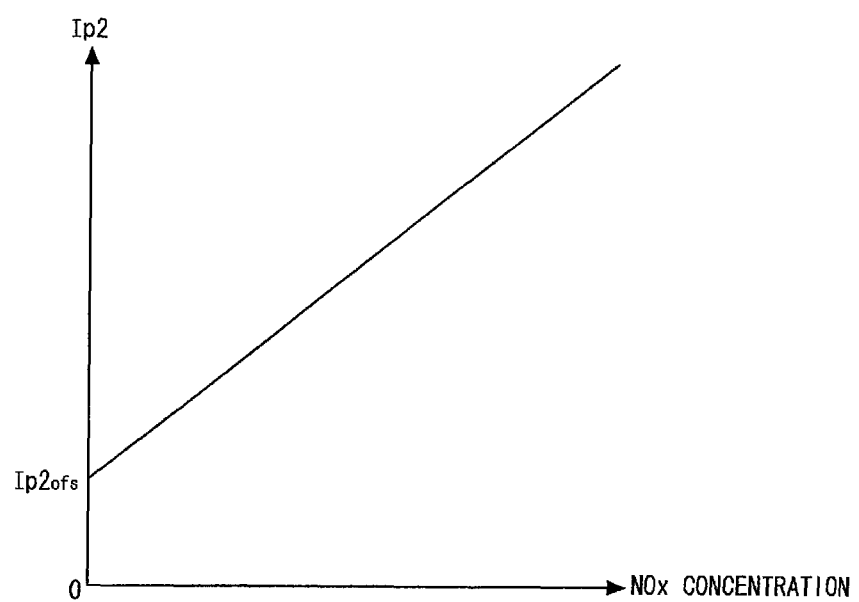
FIG. 2 is a diagram illustrating a functional relationship (sensitivity characteristics) between a pump current Ip2 and a NOx concentration.

FIG. 2 is a diagram illustrating a functional relationship (sensitivity characteristics) between the pump current Ip2 and the NOx concentration. Ideally, the value of Ip2 should be zero under a state where NOx does not exist. Actually, however, oxygen is not completely removed from the measurement gas, and a little amount of oxygen is left in the measurement gas having reached the measuring electrode. Therefore, even in the state where NOx does not exist, oxygen ion is generated by decomposition of such oxygen, to cause a current to flow. The NOx current Ip2 obtained when the NOx concentration is zero is particularly called an offset current $Ip2_{ofs}$. The sensitivity characteristics (more specifically, the offset current $Ip2_{ofs}$ and the slope of a graph) as shown in FIG. 2 are identified with respect to each individual sensor element 101, prior to usage. In an actual detection of NOx, the value of Ip2 is constantly measured, and based on the sensitivity characteristics that have been previously identified, a NOx concentration corresponding to each individual measured value is obtained.

In the sensor element 101, the oxygen partial pressure in the outside of the sensor element 101 can also be recognized by measuring the electromotive force $V_{ref}$ that is caused between the outside pump electrode 23 and the reference electrode 42.

Furthermore, in order to enhance an oxygen-ion conductivity of the solid electrolyte, the sensor element 101 includes a heater part 70 serving for a temperature adjustment for heating and keeping warm the sensor element 101. The heater part 70 includes a heater electrode 71, a heater 72, a through hole 73, a heater insulating layer 74, and a pressure diffusion hole 75.

The heater electrode 71 is an electrode formed in contact with a lower surface of the first substrate layer 1. By connecting the heater electrode 71 to an external power source, electrical power can be supplied to the heater part 70 from the outside.

The heater 72 is an electric resistor interposed between the second substrate layer 2 and the third substrate layer 3 with respect to the vertical direction. The heater 72 is connected to the heater electrode 71 via the through hole 73. The heater 72 generates heat when power is supplied from the outside through the heater electrode 71, and heats and keeps warm the solid electrolyte which forms the sensor element 101.

The heater 72 is buried over the entire area extending from the first internal space 20 to the second internal space 40, so that the temperature of the entire sensor element 101 can be adjusted at a temperature at which the solid electrolyte is activated.

The heater insulating layer 74 is an insulating layer constituted by an insulator such as alumina and formed on upper and lower surfaces of the heater 72. The heater insulating layer 74 is formed for the purpose of providing an electrical insulation between the second substrate layer 2 and the heater 72 and an electrical insulation between the third substrate layer 3 and the heater 72.

The pressure diffusion hole 75 is formed through the third substrate layer 3, and communicates with the reference gas inlet space 43. The pressure diffusion hole 75 is formed for the purpose of relieving a rise in the internal pressure which is involved in a temperature rise in the heater insulating layer 74.

<Method for Manufacturing Sensor Element>

Next, a process of manufacturing the sensor element 101 having the above-described structure will be described. In outline, in this embodiment, predetermined patterns are formed on a plurality of green sheets containing, as a ceramic component, an oxygen-ion conductive solid electrolyte such as zirconia. Then, a laminated body of the green sheets is formed, and the laminated body is cut and baked, thus preparing the sensor element 101.

Hereinafter, a case where the sensor element 101 constituted by the six layers shown in FIG. 1 is prepared will be described as an example. In such a case, six green sheets corresponding to the first substrate layer 1, the second substrate layer 2, the third substrate layer 3, the first solid electrolyte layer 4, the spacer layer 5, and the second solid electrolyte layer 6 are prepared.

Figure 3:
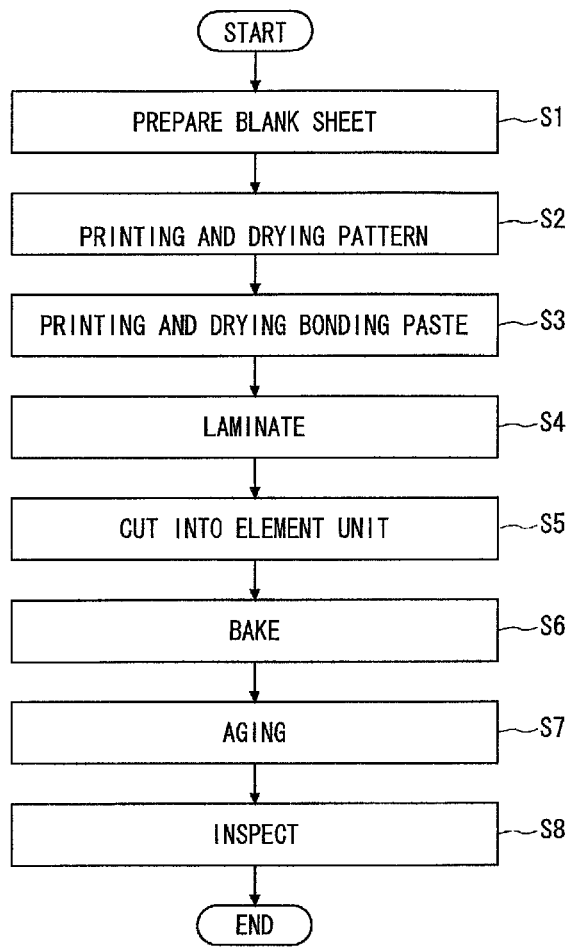
FIG. 3 is a diagram showing a process flow for preparing a sensor element 101.

FIG. 3 shows a process flow for preparing the sensor element 101. To prepare the sensor element 101, firstly, a plurality of blank sheets (not shown) which are green sheets having no pattern formed thereon are prepared (step S1). The blank sheets have a plurality of sheet holes which are used for the positioning at times of printing and laminating. The sheet holes are formed on a blank sheet before a pattern is formed thereon, through a punching process using a punching apparatus or the like. In a case of a green sheet that corresponds to a layer constituting an internal space, a penetrating portion corresponding to the internal space is also formed in advance through the same punching process or the like. Here, it is not always necessary that all the blank sheets corresponding to the respective layers of the sensor element 101 have the same thickness.

After the blank sheets corresponding to the respective layers are prepared, then a pattern-printing and drying process is performed in which various patterns are formed on the respective blank sheets (step S2). To be specific, electrode patterns for the outside pump electrode 23, the inside pump electrode 22, the auxiliary pump electrode 51, the measuring electrode 44, and the reference electrode 42, etc., the electrode protective layer 45, the air introduction layer 48, an internal wiring (not shown), and the like, are formed. On a green sheet constituting the second solid electrolyte layer 6 which serves as the uppermost surface of the sensor element 101, a cut mark is printed which is used as a reference of a cutting position when the laminated body is cut in a subsequent step.

Printing of each pattern is performed by applying a pattern-forming paste, which is prepared in accordance with each required characteristics, to the blank sheet using a known screen-printing technique. For the drying process after the printing, known drying means may be used, too. In a preferred example, the drying process is performed in the air atmosphere at a temperature of 75° C. to 90° C., for example.

After the pattern printing is completed, then a printing and drying process is performed in which a bonding paste for laminating and bonding the green sheets corresponding to the respective layers to one another is printed and dried (step S3). For the printing of the bonding paste, a known screen-printing technique may be used. For the drying process after the printing, known drying means may be used, too. It is also preferred that the drying process is performed in the air atmosphere at a temperature of 75° C. to 90° C., for example.

Subsequently, a pressure-bonding process is performed in which the green sheets having the bonding paste applied thereto are put in layers in a predetermined order and subjected to a predetermined temperature/pressure condition so that the green sheets are pressure-bonded to form a single laminated body (step S4). Specifically, the green sheets to be laminated are stacked and held onto a predetermined laminate jig (not shown) while being positioned with the sheet holes, and are heated and pressurized together with the laminate jig by a laminating machine such as a known oil-hydraulic press machine. In the heating and pressurization, the pressure, the temperature, and the time period depend on a laminating machine used. Appropriate conditions may be set to achieve a good lamination.

After the laminated body is obtained in the above-described manner, then the laminated body is cut at a plurality of portions thereof, so that a unit (referred to as an element body) for each individual sensor element 101 is cut out (step S5). The element body thus cut out is baked under a predetermined condition, and thereby evaporation of an organic component contained in the element body, sintering of the ceramic component, and additionally sintering of an electrode metal, and the like, make progress (step S6). In a preferred example, the baking is performed in the air atmosphere at a bake temperature of 1350° C. to 1400° C., for example.

An aging process (step S7) in a rich atmosphere is performed on the baked element body, for the purpose of reducing the electrode which has been oxidized in the baking. For forming the rich atmosphere, gas containing CO, $CH_4$, $C_2H_6$, $C_3H_8$, or the like, is used.

Then, the element body having gone through the aging process is subjected to an inspection step (step S8). FIG. 4 is a diagram showing a flow of the inspection step. In the inspection step, firstly, an inspection of an external appearance is performed (step S8a). In the inspection of an external appearance, for example, an element body in which a foreign material attaches to a surface is determined as NG. An element body that has passed the inspection of an external appearance is subjected to a pre-treatment (step S8b), and then subjected to an inspection of element characteristics (step S8c).

The inspection of element characteristics is an inspection of electrical characteristics that is performed before an element body having subjected to the aging process is assembled as the sensor element 101 into a main body part of the gas sensor 100. The inspection of element characteristics is performed under a state where an inspection gas is actually flowing, for the purpose of confirming that characteristics of the pumping cells and the sensor cells are within predetermined ranges that are defined as standards in advance. The pre-treatment is a treatment prior to the inspection of element characteristics. The pre-treatment is performed for the purpose of stabilizing electrodes of the sensor element. Details of the pre-treatment and the inspection of element characteristics will be described later. In the following, for simplification of the description, an element body having subjected to the aging process may be expressed simply as the sensor element 101 irrespective of whether or not the element body has passed the inspection.

An element body that has passed all the inspections is, as the sensor element 101, accommodated in a predetermined housing and assembled into a main body (not shown) of the gas sensor 100.

<Element Characteristics Inspection Apparatus>

Figure 5:
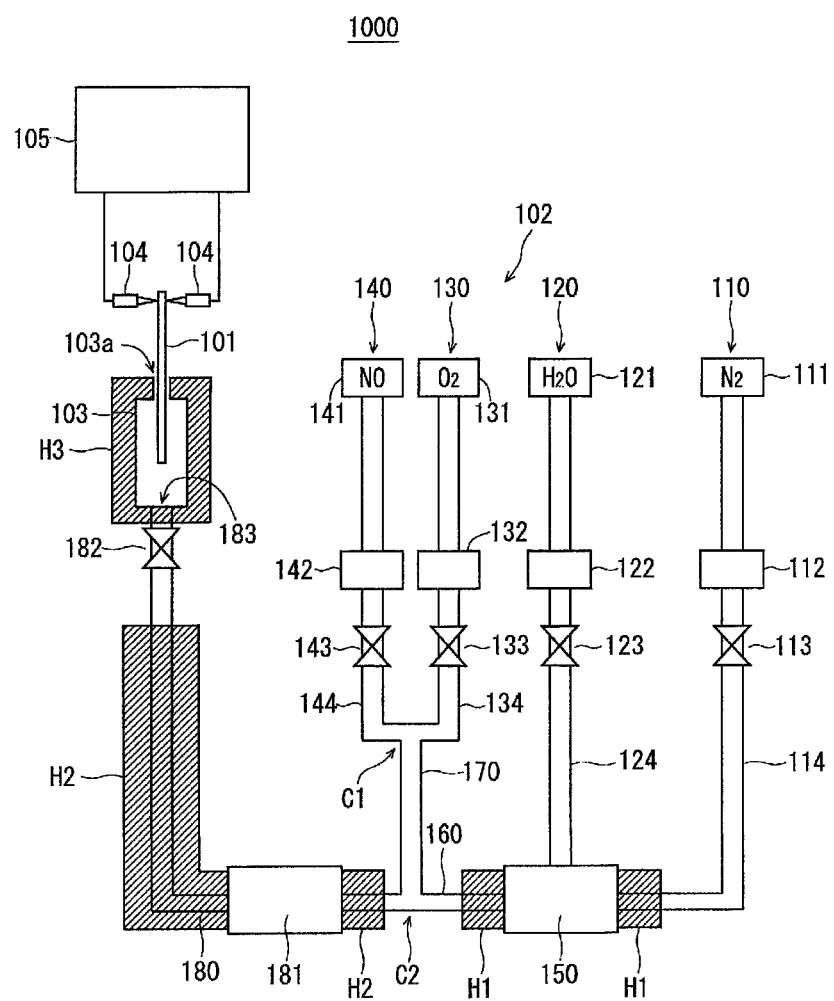
FIG. 5 is a schematic diagram illustrating an inspection apparatus 1000 that is used for inspection of element characteristics.

Next, an inspection apparatus used for the inspection of element characteristics will be described. FIG. 5 is a schematic diagram illustrating an inspection apparatus 1000 used for the inspection of element characteristics. The inspection apparatus 1000 includes a mixed gas feeder 102, a measurement chamber 103, and a measuring device 105. The mixed gas feeder 102 supplies a mixed gas mixed at a desired mixing ratio. The mixed gas is introduced from the mixed gas feeder 102 to the measurement chamber 103. The measuring device 105 is configured to perform a predetermined electrical measurement by connecting probes 104 to a predetermined position of the sensor element 101 placed in the measurement chamber 103. As the measuring device 105, a measuring instrument, or the like, capable of measurement suitable for what is to be inspected may be appropriately used.

In the example shown in FIG. 5, for simplification of the illustration, one measurement chamber 103 is connected to the mixed gas feeder 102. However, a supply pipe extending from the mixed gas feeder 102 may be branched so that a plurality of measurement chambers 103 are connected to one mixed gas feeder 102. In such a case, it is preferable that a plurality of sensor elements 101 can be measured concurrently.

In the example shown in FIG. 5, for simplification of the illustration, the probes 104 are connected to the sensor element 101 in such a manner that an end portion of the sensor element 101 is sandwiched between the two probes 104. However, in an actual case, the number of probes 104 and how the probe 104 is connected are not limited thereto. A probe 104 for voltage application, a probe 104 for current passage, and additionally a probe 104 for current detection, which are prepared properly in accordance with a specific structure of the sensor element 101 and what is to be inspected in the inspection of element characteristics, are connected to appropriate positions (terminal positions (not shown) corresponding to the respective electrodes).

The mixed gas feeder 102 includes a nitrogen supply system 110, a water supply system 120, an oxygen supply system 130, and a NO supply system 140. These supply systems have, as supply sources (chemical cylinders, tanks, or the like) of respective materials thereof, a nitrogen supply source 111, a water supply source 121, an oxygen supply source 131, and a NO supply source 141, respectively. Mass flow controllers 112, 122, 132, and 142 for adjusting flow rates, and valves 113, 123, 133, and 143 are provided in the middle of the respective supply paths 114, 124, 134, and 144.

Among these four supply systems, a supply path 114 of the nitrogen supply system 110 and a supply path 124 of the water supply system 120 are connected to a vaporizer 150. In the vaporizer 150, water supplied from the water supply system 120 is vaporized into water vapor which is then mixed with nitrogen supplied from the nitrogen supply system 110. A heater H1 is attached to the vaporizer 150, and is configured to heat the atmosphere inside the vaporizer 150. The heater H1 is controlled by a temperature controller (not shown).

In the vaporizer 150, the water vapor and the nitrogen are mixed while the heater H1 is heating the atmosphere of the vaporizer 150 to approximately 100° C. to 120° C. This can suitably prevent the water from remaining without being vaporized. A mixed gas of the water vapor and the nitrogen flows out of the vaporizer 150 into a first preliminary mixture path 160.

On the other hand, the oxygen supply system 130 and the NO supply system 140 meet at a junction C1, so that a mixed gas of the oxygen and the NO supplied from the oxygen supply system 130 and the NO supply system 140, respectively, flows in a second preliminary mixture path 170.

Furthermore, the second preliminary mixture path 170 meets the first preliminary mixture path 160 at a junction C2. Thereby, a mixed gas of the gases supplied from the first and second preliminary mixture paths 160 and 170, in other words, a mixed gas of all the gases supplied from the four supply systems, flows in a mixed gas supply path 180. In the mixed gas supply path 180, a gas mixer 181 is provided near the junction C2, so that the mixed gas having being sufficiently mixed by the gas mixer 181 is supplied to the measurement chamber 103 from a supply port 183 provided at an end of the mixed gas supply path 180. A valve 182 is provided in the mixed gas supply path 180, so that the valve 182 adjusts a flow rate of the mixed gas supplied to the measurement chamber 103.

Although in a preferred example, a so-called static mixer (static type mixer) is used as the gas mixer 181, a dynamic mixer may also be adoptable.

A heater H2 is attached to the mixed gas supply path 180. Preferably, a heater H3 is provided to the measurement chamber 103. The heater H2 and the heater H3 are controlled by a temperature controller (not shown). The heater H2 and the heater H3 maintain the temperature of the atmosphere of the measurement chamber 103, at approximately 100° C. to 120° C.

One end of the measurement chamber 103 is connected to the supply port 183 of the mixed gas feeder 102, and the other end thereof forms an opening 103a communicating with the outside. Through the opening 103a, the sensor element 101 is inserted into the measurement chamber 103. In the measurement made by the measuring device 105, the sensor element 101 is positioned such that its side having the gas inlet 10 is inserted into the measurement chamber 103 and its side having terminal electrodes 151 and 152 protrudes out of the measurement chamber 103. Such a state is shown in FIG. 5.

In FIG. 5, a supply route extending from the nitrogen supply source 111 through the supply path 114 and the first preliminary mixture path 160 to the supply port 183 of the mixed gas supply path 180 has a squared C-like shape. This illustration is merely for the sake of convenience, and does not show an actual pipe layout of the mixed gas feeder 102.

<Inspection of Element Characteristics>

Next, the inspection of element characteristics that is performed by using the above-described inspection apparatus 1000 will be described. In outline, the inspection of element characteristics is performed as follows. The sensor element 101 is set in the measurement chamber 103 of the inspection apparatus 1000, and then the NOx current Ip2 of the sensor element 101 is measured while an inspection gas whose NOx concentration is already known is flowing through the measurement chamber 103.

Figure 6:
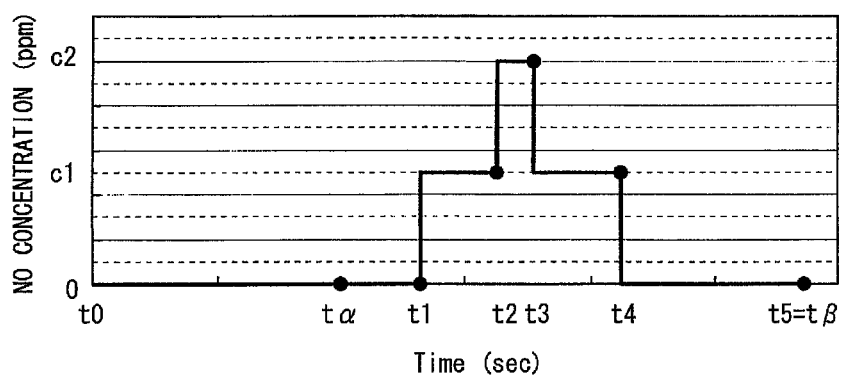
FIG. 6 is a diagram showing an example of a concentration profile of an inspection gas that is introduced into the inspection apparatus 1000 in the inspection of the element characteristics.

FIG. 6 is a diagram showing an example of a concentration profile of the inspection gas that is introduced into the inspection apparatus 1000 in the inspection of the element characteristics. In a case shown in FIG. 6, until a predetermined time t1 elapses from a start of the inspection (time 0), an inspection gas whose NOx concentration is zero is introduced. Then, in a time period from time t1 to time t2, an inspection gas whose NOx concentration is c1 (ppm) is introduced. Then, in a time period from time t2 to time t3, an inspection gas whose NOx concentration is c2 (ppm) is introduced (c2>c1). Then, in a time period from time t3 to time t4, an inspection gas whose NOx concentration is c1 (ppm) is introduced again. After elapse of time t4, an inspection gas whose NOx concentration is zero is introduced. At time t5, the inspection ends.

Figure 7:
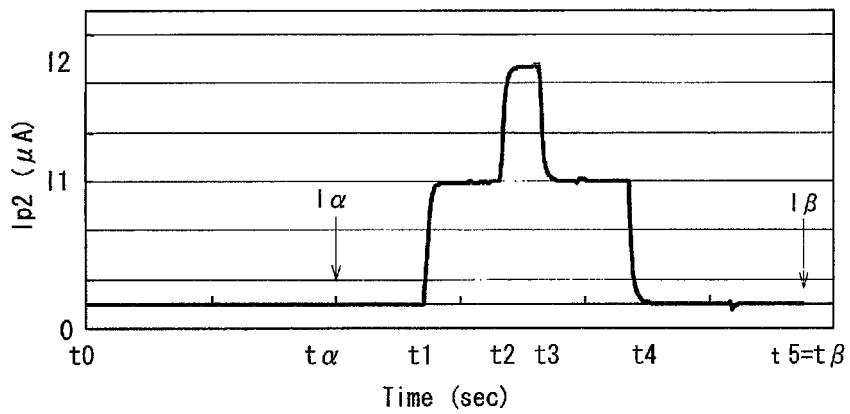
FIG. 7 is a diagram illustrating a profile of a NOx current Ip2, which is obtained by introducing the inspection gas having the concentration profile shown in FIG. 6.

FIG. 7 is a diagram illustrating a profile of the NOx current Ip2, which is obtained by introducing the inspection gas having the concentration profile shown in FIG. 6. In the inspection of element characteristics, in a case where the obtained profile of the NOx current Ip2, for example, as shown in FIG. 7 satisfies a predetermined acceptability criterion, the sensor element 101 (element body) that has been inspected is determined as an acceptable product.

<Pre-Treatment and Effects Thereof>

Next, a pre-treatment performed in this embodiment will be described.

As described above, each of the electrodes of the sensor element 101 is formed through the baking which is performed in the course of manufacturing the sensor element 101. At this time, each of the electrodes is oxidized to a certain degree. Therefore, in order to reduce the oxidized electrode, the aging process is performed. However, after the aging process, a rich component such as CO, $CH_4$, $C_2H_6$, or $C_3H_3$ may adsorb to and remain in the measuring electrode 44 and the electrode protective layer 45 that covers the measuring electrode 44 (hereinafter, also referred to as the measuring electrode 44 and the like).

If the inspection of element characteristics is performed under a state where such a rich component is attached, decomposition of the rich component occurs irregularly during the inspection in which occurrence of only the decomposition of NOx is assumed. This may hinder the decomposition of NOx. As a result, the inspection progresses under an unstable state in which the oxygen pumping ability of the electrochemical pumping cell, the NOx reduction ability of the measuring electrode, and the like, are not constant. In such a case, additionally, no reproducibility is obtained in the value of the NOx current Ip2 in the state where no mixed gas is flown.

The degree of attaching of the rich component to the measuring electrode 44 and the like varies among individual sensor elements 101 and individual electrodes. This means that the initial state of the measuring electrode 44 differs among individual sensor elements 101. To suppress a variation in the quality of the sensor elements 101, it is preferable that an individual difference about the state of the measuring electrode 44 is small at least in the same lot.

In view of the above, in this embodiment, a pre-treatment for stabilizing the measuring electrode 44 is performed prior to the inspection of element characteristics.

Here, the pre-treatment in this embodiment means a process of, in outline, applying a voltage between the outside pump electrode 23 and the measuring electrode 44 of the sensor element 101 to thereby forcibly decompose and remove the rich component that is attached to the measuring electrode 44 and the like.

In this embodiment, a state where the pre-treatment exerts its effects means, in a qualitative sense, a state where the measuring electrode 44 is stabilized by removal of the rich component from the measuring electrode 44 and the like described above. However, an actual criterion for the determination may be that, in the inspection of element characteristics performed after the pre-treatment, the absolute value of a difference in the values of the NOx current Ip2 before and after the introduction of the inspection gas containing NOx is 0.02 µA or less. Hereinafter, this will be referred to as a pre-treatment criterion. When the pre-treatment criterion is satisfied, it can be considered that the state of the measuring electrode 44 having subjected to the inspection of element characteristics is substantially the same as the state thereof before the inspection.

In a case where the pre-treatment criterion is adopted, in a strict sense, as for the sensor element in which no rich component has adsorbed before the pre-treatment, it is determined that the effects of the pre-treatment are exerted, even though the effects have actually not been exerted. However, there is no problem in including such a case. This is because, as long as the rich component does not adsorb, a defect that is the problem in this embodiment does not occur in the first place. Actually, however, it is considered that such a case very rarely occurs.

For example, as shown in FIGS. 6 and 7, in a case where the relationship of −0.02 µA≤ΔI≤0.02 µA is established in a difference value ΔI=Iα−Iβ between a value Iα of the NOx current Ip2 obtained at a time tα that is a predetermined time period (for example, 60 seconds) prior to the time t1 at which the inspection gas containing NOx is started to flow and a value Iβ of the NOx current Ip2 obtained at a time tβ that is a time t5 when the inspection is terminated, or in a case where the relationship of |ΔI|≤0.02 µA is established in the absolute value |ΔI|, it can be determined that the pre-treatment exerts its effects. Needless to say, this is merely an example, and another pre-treatment criterion may be set in accordance with the performance required of the sensor element 101.

Figure 8:
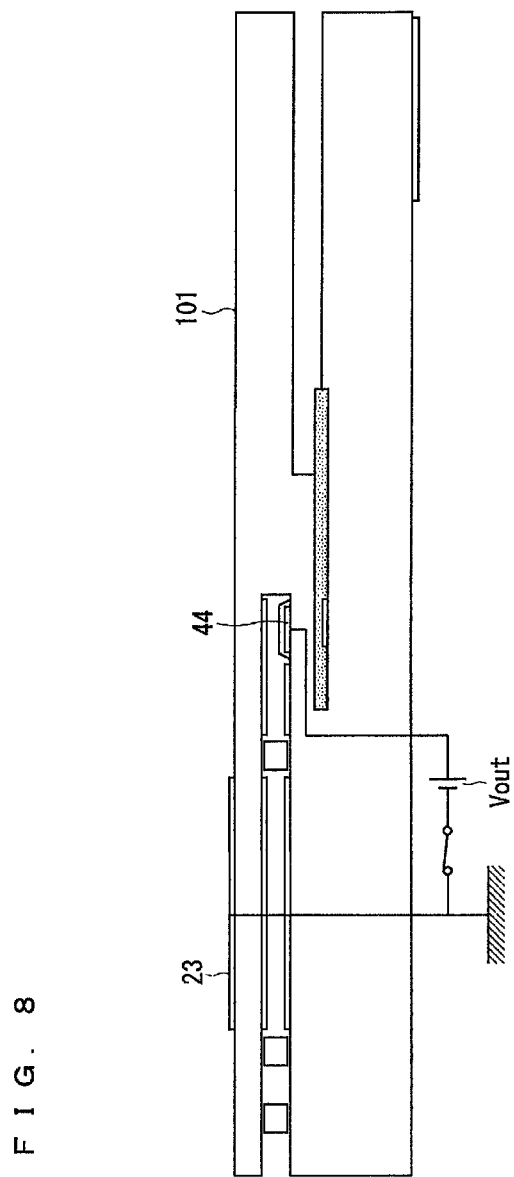
FIG. 8 is a diagram showing an outline of a pre-treatment that is performed on the sensor element 101.

FIG. 8 is a diagram showing an outline of the pre-treatment that is performed on the sensor element 101 (more strictly, the element body having passed the inspection of an external appearance) in this embodiment. In FIG. 8, the sensor element 101 is illustrated in a simplified form. In FIG. 8, for simplification of the illustration, an external power source Vout is directly connected to the outside pump electrode 23 and the measuring electrode 44. Actually, however, this connection is made at a terminal position (not shown) corresponding to each electrode.

Figure 9:
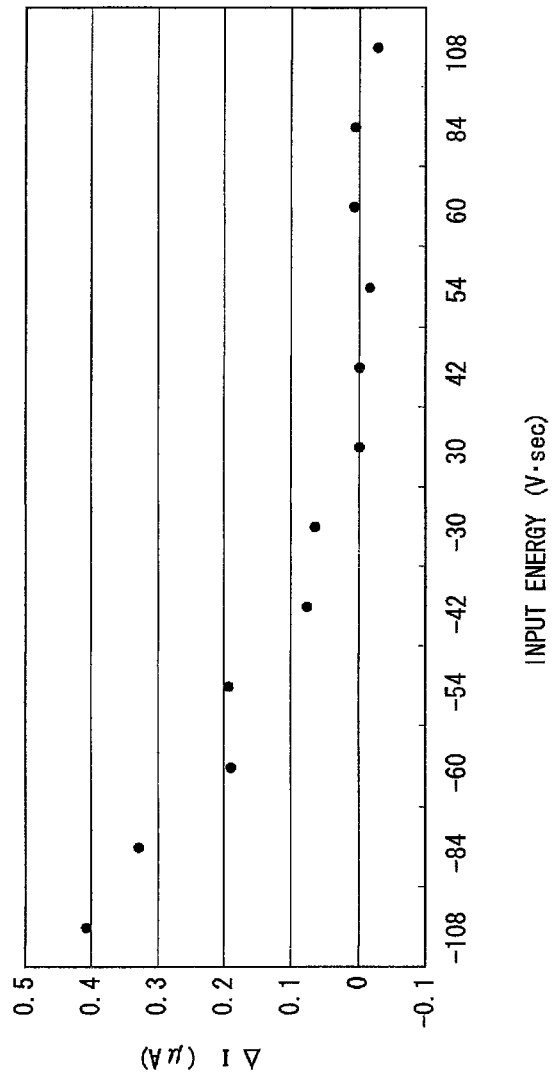
FIG. 9 is a diagram showing the relationship between an input energy and a difference value ΔI, which is obtained in a case where the value of a voltage applied between an outside pump electrode 23 and a measuring electrode 44 and a time period during which the voltage is applied are varied.

FIG. 9 is a diagram showing the relationship between an input energy and the difference value $\Delta I$, which is obtained in a case where the value of a voltage applied between the outside pump electrode 23 and the measuring electrode 44 and a time period during which the voltage is applied are varied. The input energy is represented by the product of the value of the applied voltage and the time period. Here, when a voltage is applied between the outside pump electrode 23 and the measuring electrode 44 so as to cause oxygen to be pumped out from the internal space, the applied voltage is positive, and when a voltage is applied between them so as to cause oxygen to be pumped into the internal space, the applied voltage is negative. Accordingly, in FIG. 9, the input energy is negative when the applied voltage is negative.

FIG. 9 reveals that, when the applied voltage is positive, the value of the difference value $\Delta I$ is close to zero. Therefore, in the voltage application at a time of the pre-treatment, it is preferable that the external power source Vout for the inspection is a DC power source, and the outside pump electrode 23 is connected to a negative electrode of the external power source Vout, and the measuring electrode 44 is connected to a positive electrode of the external power source Vout, as shown in FIG. 8. At this time, the outside pump electrode 23 is preferably grounded. A manner of applying the voltage in the pre-treatment is not limited thereto, and an alternating voltage or a pulse voltage may be applied. However, from the viewpoint of effectiveness, it is preferable to apply a DC voltage in the above-described manner.

When the voltage is applied between the outside pump electrode 23 and the measuring electrode 44 in the manner shown in FIG. 8, the rich component such as $CO$, $CH_4$, $C_2H_6$, or $C_3H_8$, which has adsorbed to the measuring electrode 44 and the like during the aging process, is electrically decomposed. As a result, a state where the rich component that has adsorbed to the measuring electrode 44 and the like is decomposed and removed is achieved.

However, a state of attaching of the rich component may vary among the sensor elements 101. Therefore, ideally, it is desirable that a pre-treatment condition suitable for satisfying the pre-treatment criterion described above is set for each individual sensor element 101. However, from the viewpoint of the throughput and costs, it is not practical to take such one-to-one correspondence in a mass production process. Thus, in this embodiment, the pre-treatment condition is set for each manufacturing lot. This enables at least 85% of the sensor elements 101 belonging to the same lot to satisfy the pre-treatment criterion. Setting of a specific condition may be set based on, for example, a result of extracting a plurality of sensor elements 101 belonging to the same manufacturing lot and then performing the pre-treatment under a state where the applied voltage and the time period of the application are varied.

Figure 10:
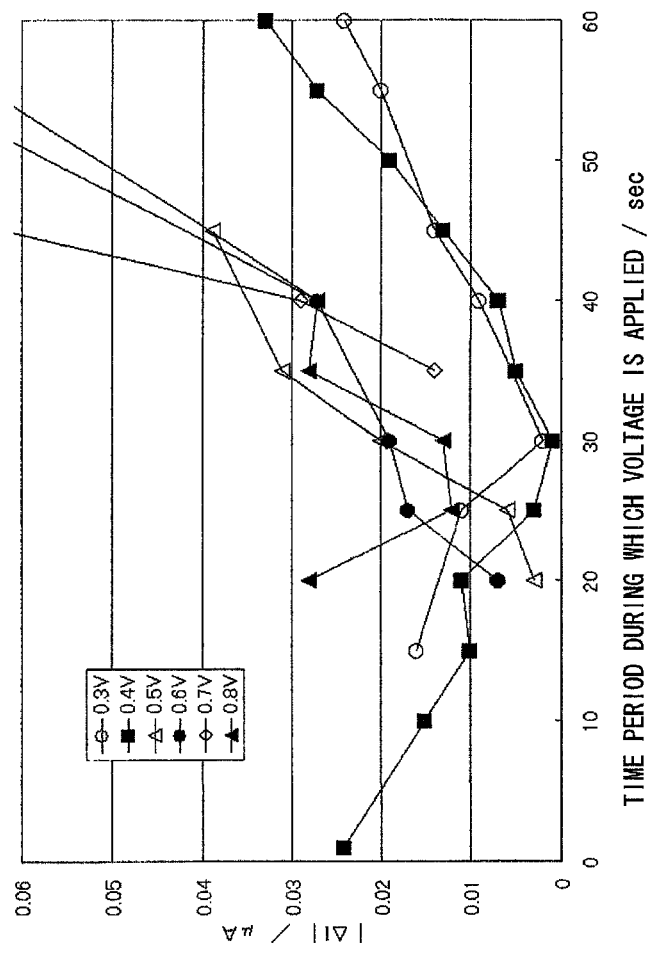
FIG. 10 is a diagram plotting, with respect to a plurality of sensor elements 101 belonging to the same manufacturing lot, the value of obtained at a time when the pre-treatment is performed under a state where the applied voltage and the time period of the application are varied

FIG. 10 is a diagram plotting, with respect to a plurality of sensor elements 101 belonging to the same manufacturing lot, the value of $|\Delta I|$ obtained at a time when the pre-treatment is performed under a state where the applied voltage and the time period of the application are varied, for the purpose of setting the pre-treatment criterion.

In a result shown in FIG. 10, when the applied voltage is 0.4V, the pre-treatment criterion is satisfied over a relatively wide range of the time period of the application, as compared with other applied voltages. When the time period of the application is 30 sec, the value is minimum. In this case, such a judgment is made that it is preferable that the pre-treatment is performed on the sensor elements 101 in this manufacturing lot under a pre-treatment condition that the applied voltage is 0.4V and the time period of the application is 30 sec.

Figure 11:
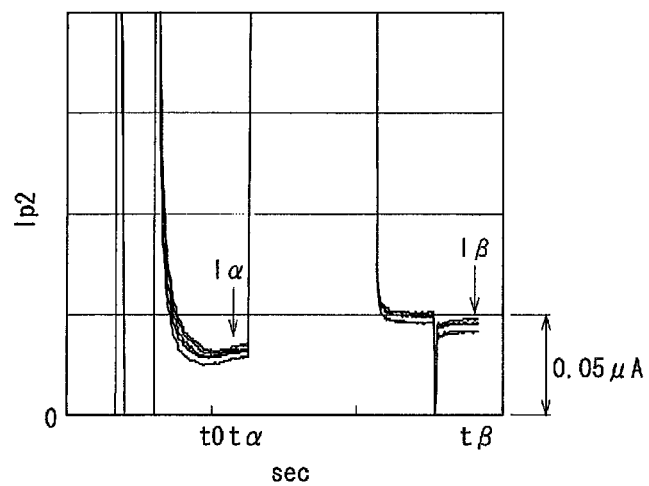
FIG. 11 is a diagram showing, on an enlarged scale, a portion of the profile of the NOx current Ip2 in the vicinity of Ip2=0, which is obtained in a case where the sensor element 101 having the pre-treatment performed thereon is inspected for its element characteristics.
Figure 12:
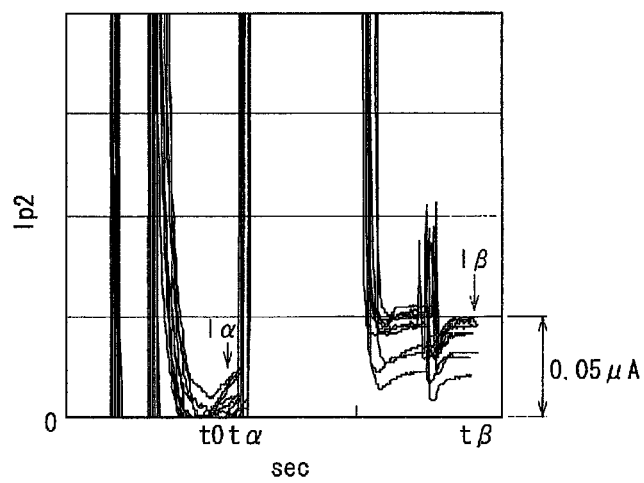
FIG. 12 is a diagram showing, on an enlarged scale, a portion of the profile of the NOx current Ip2 in the vicinity of Ip2=0, which is obtained in a case of inspecting the element characteristics without performing the pre-treatment.

FIGS. 11 and 12 are diagrams showing the effects of the pre-treatment. To be specific, FIG. 11 is a diagram showing, on an enlarged scale, a portion of the profile of the NOx current Ip2 in the vicinity of Ip2=0, which is obtained in a case where the sensor element 101 having the pre-treatment performed thereon is inspected for its element characteristics. FIG. 12 is a diagram showing, on an enlarged scale, a portion of the profile of the NOx current Ip2 in the vicinity of Ip2=0, which is obtained in a case of inspecting the element characteristics without performing the pre-treatment, for the comparison.

Each of FIGS. 11 and 12 shows a result of inspecting the element characteristics of twelve sensor elements 101. The pre-treatment condition was set such that the applied voltage was 1V and the time period of the application was 60 sec. In FIGS. 11 and 12, the value of the NOx current Ip2 fluctuates at a time point before the time t0 and immediately before the time tβ. The reason therefore is not relevant to the inspection of element characteristics that is the subject of this embodiment.

Comparing FIGS. 11 and 12, firstly, there is a large difference in the stability of the NOx current Ip2 in a period between the time t0 and the time tα, which is before the introduction of the inspection gas containing NOx is started, and in the vicinity of the time tβ, at which the inspection of element characteristics is terminated. That is, the fluctuation is smaller when the pre-treatment is performed than when the pre-treatment is not performed. Additionally, a variation in the value among lots is smaller when the pre-treatment is performed. In the case shown in FIG. 11, the pre-treatment criterion is satisfied in all the sensor elements 101.

The above-described result indicates that performing the pre-treatment is effective in stabilizing the measuring electrode 44 and suppressing a variation among individual elements. If the inspection of element characteristics is performed even though electrode is not yet stabilized, a sensor element 101 that would be determined to be a non-defective product under a stabilized state is actually determined to be a defective product. Therefore, performing the pre-treatment is effective in preventing such an erroneous decision.

If sensitivity characteristics are determined in a state where there is the fluctuation as shown in FIG. 12, the sensitivity characteristics may not be reproduced during the subsequent use of the gas sensor 100. Therefore, a NOx concentration calculated based on the sensitivity characteristics does not always have a sufficient reliability. In a case where the pre-treatment is performed, the fluctuation as shown in FIG. 12 is not seen, and therefore sensitivity characteristics can surely be determined with a reliability.

It has been confirmed that, even when the pre-treatment is not performed on a sensor element 101 as shown in FIG. 12, the condition of the electrode is eventually stabilized if the sensor element 101 is driven for a long time in the course of the inspection of element characteristics. However, since a time period until such a stabilized condition is obtained varies among individual sensor elements 101, this method is not suitable for the inspection of element characteristics which has to be performed in a routine in as short a time as possible. Therefore, this method is inefficient.

Focusing only on the stabilization of the electrode, in principle, the same object can be attained by performing the pre-treatment after the sensor element 101 not subjected to the above-described pre-treatment is assembled in the main body of the gas sensor 100. However, it should be noted that there is a risk that a sensor element 101 which is a defective product and therefore should be removed in an early stage may be allowed to reach an assembling step in a subsequent stage.

One of methods that aim at the same effects as the effects of the pre-treatment of this embodiment is a method as disclosed in Japanese Patent Application Laid-Open No. 2011-145285, in which, prior to inspecting element characteristics, a process (hereinafter, referred to as a gas pre-treatment) of driving a sensor element for a predetermined time period in a mixed gas atmosphere similar to the actual usage environment is performed as a pre-treatment. FIGS. 13 and 14 are histograms of the value of ΔI, which are obtained in a case of inspecting the element characteristics after performing the pre-treatment of this embodiment and in a case of inspecting the element characteristics after performing the gas pre-treatment. The pre-treatment condition was such that the applied voltage was 1V and the time period of the application was 60 sec. A time period during which the sensor element 101 was driven in the gas pre-treatment was also set to be 60 sec. In both of the cases, the evaluation was made on 300 sensor elements 101.

Comparing FIGS. 13 and 14, there is a tendency that the value of |ΔI| is smaller when the pre-treatment according to this embodiment is performed than when the gas pre-treatment is performed. More specifically, in a case where the pre-treatment according to this embodiment is performed, the sensor elements 101 that satisfied the pre-treatment criterion accounted for 98% of all the evaluated sensor elements, while in a case of the gas pre-treatment, the sensor elements 101 that satisfied the pre-treatment criterion accounted for only 76%. Even in a case of the gas pre-treatment, if the time period of driving the sensor element 101 prolonged, the percentage of the sensor elements 101 that satisfy the pre-treatment criterion is increased. However, such a result indicates that the pre-treatment can more efficiently stabilize the measuring electrode 44 than the gas pre-treatment.

As described above, in this embodiment, a voltage is applied between the outside pump electrode and the measuring electrode before the inspection of element characteristics which is inspection of electrical characteristics of the sensor element is performed. Thereby, the inspection of element characteristics can be performed under a state where the rich component attached to the measuring electrode and the like is forcibly decomposed and removed so that the condition of the measuring electrode is stabilized. This can prevent, in the inspection of element characteristics, occurrence of the erroneous decision which determines that a sensor element which should be determined to be a non-defective product is a defective product. Additionally, the sensitivity characteristics can be surely determined with a reliability. Thus, in this embodiment, the production yield can be improved, and the NOx sensor having a high reliability can be achieved.

What is claimed is:

1. A method for manufacturing a sensor element for use in a gas sensor that measures a concentration of a predetermined gas component in a measurement gas, said sensor element comprising an electrochemical pumping cell including:
   an oxygen-ion conductive solid electrolyte layer;
   a pump electrode of a pair of pump electrodes, which is formed on an outermost exterior surface of said oxygen-ion conductive solid electrolyte layer; and
   a measuring electrode of a pair of measuring pump electrodes, which is formed in a space provided inside said oxygen-ion conductive solid electrolyte layer,
   said method comprising the steps of:
   a) forming, by printing, a wiring pattern of a conductive paste on a green sheet containing, as a main component, ceramic which is an oxygen-ion conductive solid electrolyte, said wiring pattern including portions serving as said pump electrode and said measuring electrode;
   b) laminating a plurality of green sheets that have been subjected to said step a), and integrating said plurality of green sheets;
   c) cutting out a plurality of element bodies from a laminated body obtained by said step b);
   d) baking the element body cut out by said step c);
   e) heating the element body having been subjected to said step d), in a reducing rich atmosphere so as to manufacture said sensor element;
   f) performing a pre-treatment, by an external power source, applying a voltage between said pump electrode and said measuring electrode included in the element body having been subjected to said step e), to thereby decompose and remove a rich component of said step e) attached to said measuring electrode; and
   g) inspecting electrical characteristics of the element body having been subjected to said step f).

2. The method for manufacturing a sensor element according to claim 1, wherein
   in said step F), a DC voltage is applied between said pump electrode and said measuring electrode under a state where said pump electrode is connected to a negative electrode of said external power source and said measuring electrode is connected to a positive electrode of said external power source.

3. A method for inspecting electrical characteristics of a sensor element for use in a gas sensor that measures a concentration of a predetermined gas component in a measurement gas, said method comprising the steps of:
   providing a manufactured sensor element, said sensor element comprising an electrochemical pumping cell including
   an oxygen-ion conductive solid electrolyte layer,
   a pump electrode of a pair of pump electrodes, which is formed on an outermost exterior surface of said oxygen-ion conductive solid electrolyte layer, and
   a measuring electrode Of a pair of measuring pump electrodes, which is formed in a space provided inside said oxygen-ion conductive solid electrolyte layer; and
   applying a pre-treatment, by an external power source, a voltage between said pump electrode and said measuring electrode included in said sensor element, to thereby decompose and remove a rich component attached to said measuring electrode, and then inspecting electrical characteristics.

4. The method for inspecting electrical characteristics of a sensor element according to claim 3, wherein
   in decomposing and removing said rich component, a DC voltage is applied between said pump electrode and said measuring electrode under a state where said pump electrode is connected to a negative electrode of said external power source and said measuring electrode is connected to a positive electrode of said external power source.

5. A method for performing a pre-treatment on a sensor element for use in a gas sensor that measures a concentration of a predetermined gas component in a measurement gas, said pre-treatment being performed prior to an inspection of electrical characteristics, said method comprising the steps of:
   providing a manufactured sensor element, said sensor element comprising an electrochemical pumping cell including
      an oxygen-ion conductive solid electrolyte layer,
      a pump electrode of a pair of pump electrodes, which is formed on an outermost exterior surface of said oxygen-ion conductive solid electrolyte layer, and
      a measuring electrode of a pair of measuring pump electrodes, which is formed in a space provided inside said oxygen-ion conductive solid electrolyte layer; and
   applying said pre-treatment, by an external power source, a voltage between said pump electrode and said measuring electrode included in said sensor element, to thereby decompose and remove a rich component attached to said measuring electrode.

6. The method for performing the pre-treatment on a sensor element according to claim 5, wherein
   in decomposing and removing said rich component, a DC voltage is applied between said pump electrode and said measuring electrode under a state where said pump electrode is connected to a negative electrode of said external power source and said measuring electrode is connected to a positive electrode of said external power source.

* * * * *